United States Patent [19]

Kojima et al.

US005756542A

[11] Patent Number: 5,756,542

[45] Date of Patent: May 26, 1998

[54] OINTMENT-LIKE PREPARATION COMPRISING ALLYL ISOTHIOCYANATE FOR THE PROTECTION OF A TREE AND METHOD OF PROTECTING A TREE

[75] Inventors: Takeshi Kojima, 3, Anshudounogo-cho, Yamashina-ku, Kyoto-shi, Kyoto-fu, 607; Akinori Kimura, Aomori-ken, both of Japan

[73] Assignee: Takeshi Kojima, Kyoto-fu, Japan

[21] Appl. No.: 481,248

[22] PCT Filed: Oct. 26, 1994

[86] PCT No.: PCT/JP94/01793

§ 371 Date: Jun. 23, 1995

§ 102(e) Date: Jun. 23, 1995

[87] PCT Pub. No.: WO95/11591

PCT Pub. Date: May 4, 1995

[30] Foreign Application Priority Data

Oct. 26, 1993 [JP] Japan ................................ 5-289939

[51] Int. Cl.$^6$ .................... A01N 25/28; A01N 35/06; A01N 47/46

[52] U.S. Cl. .................... 514/514; 514/515; 514/690; 47/11

[58] Field of Search ..................... 514/514, 515, 514/690

[56] References Cited

U.S. PATENT DOCUMENTS

| | | | |
|---|---|---|---|
| 4,228,124 | 10/1980 | Kashihara et al. | 422/36 |
| 4,659,739 | 4/1987 | Yoshioka et al. | 514/555 |

OTHER PUBLICATIONS

*Farm Chemicals Handbook* p. C68, 1987.

*Primary Examiner*—S. Mark Clardy
*Attorney, Agent, or Firm*—Spencer & Frank

[57] ABSTRACT

A method of protecting a tree including removing parts of the tree which are one of susceptible to necrosis from pathogenic microbes or affected by necrosis and leaving exposed tree surfaces; and applying to the exposed tree surfaces a composition which is an ointment and which is effective to protect a tree against disease which includes allyl isothiocyanate; vinyl acetate resin as a spreading agent; water-based colored paint; metallic powder which is finely divided and which is one of iron or ferrous oxide; and pH regulating agent. The allyl isothiocyanate may be encapsulated by a coating material.

15 Claims, No Drawings

5,756,542

1

OINTMENT-LIKE PREPARATION COMPRISING ALLYL ISOTHIOCYANATE FOR THE PROTECTION OF A TREE AND METHOD OF PROTECTING A TREE

BACKGROUND OF THE INVENTION

This application has been filed under 35 USC 371 from International Application PCT/JP94/01793, filed Oct. 26, 1994.

1. Field of the Invention

This invention relates to an ointment-like preparation for protecting a tree such as an apple or a pear tree by applying it to the tree to prevent pathogenic microbes such as *Valsa ceratosperma* from invading the tree and expanding the colonies settled there to eventually destroy it through wilting. It also relates to an improved method of protecting a tree.

Additionally, the present invention relates to an ointment-like preparation for accelerating the growth of a grafted tree or of shoots of the root of a tree that has been cut midway for transplantation.

2. Description of the Related Art

Orchard farming on apples and other fruits is a major industry in northern regions of Japan including Hokkaido, Aomori, Akita, Iwate and Nagano. While bactericides and pesticides are used at a high rate on orchard trees because such trees are susceptible to diseases by microbes and insects, they can give rise to serious environmental problems including polluted soil and water. These problems are now found everywhere in the world. The incidence of necrosis due to microbes and insects in apple orchards is particularly high and practically all the apple orchards in Japan are currently suffering from it. Plant necrosis include dieback that gives rise to pale brown spots on the exposed areas of trimmed branches and on peduncles and fresh twigs of an affected tree and blight that produces diseased spots on the trunk and major branches of a suffering tree that become wet and dark in early spring. They are both caused by pathogenic microbes.

Therefore, efforts have been made for the prevention of plant necrosis.

Traditional and conventional techniques for protecting apple trees and other orchard trees against necrosis include the following.

Doromaki (mudding and wrapping) method: With this technique, each area affected by blight including the arease is totally covered by mud to a thickness of 3 to 5 cm and then by a sheet of vinyl or polyethylene to prevent the wet mud from drying and then left under this covered condition for about a year.

Medicament application method: With this method, each part affected by blight is removed by cutting and an ointment-like medicament such as TOPZIN M paste or BEFRAN is applied to the exposed area including the surrounding areas for a plurality of times.

However, the doromaki method involves cumbersome operations of applying mud and covering the applied area with a sheet of vinyl or polyethylene and hence is time consuming.

While application of a medicament is a relatively simple operation by itself, it should be repeated for a number of times until the harvest and therefore, if the medicament is diluted, it can eventually contaminate soil and water in the surroundings to the detriment of the environment that might have been already polluted to a certain extent by a variety of different chemicals used for raising orchard trees.

2

What is worse, known medicaments that have been proposed to date for this method are not particularly effective for the protection of orchard trees.

While grafting may be an effective way for the prevention of plant necrosis, it requires a rigorous selection of finding a matching scion in order to make it genetically viable and therefore it is not a widely accepted practice.

Another effective way for the prevention of plant necrosis may be transplanting. However, for transplanting a tree, considerable part of the root hairs are inevitably cut to make the tree less active in sucking water from the soil.

In view of these and other problems in the conventional techniques in this field of technology, it is therefore a first object of the invention to provide an ointment-like preparation that can be used easily on a tree and effectively vitalize it until it actively reproduces the bark and the root if applied to it only for a limited number of times. A second object of the invention is to provide a method of protecting a tree against disease.

SUMMARY OF THE INVENTION

According to an aspect of the invention, the above first object is achieved by providing an ointment-like preparation for the protection of a tree comprising a mixture of an isothiocyanate ester, such as allyl isothiocyanate or hinokitiol, a vinyl acetate resin, a coloring water paint, a powdery metal and a pH regulating agent. According to another aspect of the invention, the above second object is achieved by providing a method of protecting a tree comprising removing the parts of the tree affected by necrosis and applying an ointment-like preparation for the protection of the tree containing a mixture of an isothiocyanate ester such as allyl isothiocyanate or hinokitiol, a vinyl acetate resin, a coloring water paint, a powdery metal and a pH regulating agent to the exposed areas of the tree after removing the affected parts.

For the purpose of the invention, an isothiocyanate ester, such as allyl isothiocyanate or hinokitiol, is preferably encapsulated into microcapsules by a known technique in order to keep it under a chemically stabilized condition and suppress its irritating flavor.

Allyl isothiocyanate ($CH_2$=$CHCH_2N$=$C$=$S$) is a chemical that is liquid at room temperature (25° C.) and harmless to the human body. It is authorized to be used for food as an additive in the United States and also has long been used as an additive in Japan to be used for green radish and mustard.

Allyl isothiocyanate has a strong and irritating flavor that can stun people on the floor of the processing plant if used without any precautionary measures. Another drawback of the substance is that it can become chemically unstable with time.

However, these drawbacks of the irritating flavor and the chemical instability can be effectively overcome by encapsulating it into microcapsules.

Hinokitiol ($C_{10}H_{12}O_2$) which is also called 4-isopropyltropolone (or β-thujapricin) is a substance that can be extracted from refined oil of white cedar and has a bactericidal effect. For the purpose of the invention, it is preferably encapsulated into microcapsules in order to make it chemically stable for a prolonged period of time.

An isothiocyanate ester, such as allyl isothiocyanate or hinokitiol, can be encapsulated into microcapsules by any of the known methods including one that uses cyclodextrin as an enclosure compound (Japanese Patent Laid-open Nos. 03-224437, 05-155723 and 05-176733) and one with which fine particles of allyl isothiocyanate or hinokitiol are dispersed into aqueous solution of a mixture of a urea formaldehyde resin prepolymer, a water soluble cationic urea resin and an anionic surfactant and adding an acidic catalyst to form a coating on the fine particles (Japanese Patent Publication No. 03-34649). The encapsulated material is preferably used at a rate of 0.05 to 1.0% by weight.

While water paints that can be used for the purpose of the invention include water soluble polyester resin type paints and water soluble acrylic resin type paints, a coloring acrylic resin type paint is preferably used in order to protect the surface, to which the preparation is applied, from exposure to light. For the purpose of the invention, powdery ferrous oxide at a rate of 1 to 10% by weight is preferably used as a powdery metal.

A vinyl acetate resin (having an enhanced water absorbing power) is used as a spreading agent at a rate of 70 to 90% by weight in a preparation according to the invention. Acetic acid at a rate of 1 to 10% by weight is preferably used as a pH regulating agent in a preparation according to the invention.

Of an ointment-like preparation according to the invention and having a composition as described above, the isothiocyanate or hinokitiol effectively suppresses the activity of pathogenic microbes that cause necrosis.

The vinyl acetate resin effectively covers the surface of the tree to which the preparation is applied to protect it against adverse climatic effects and, at the same time, operates as an agent for spreading other components.

The coloring water paint screens rays of sunlight trying to strike the surface of the tree to which the preparation is applied and, at the same time, protects the tree.

The powdery metal and acetic acid which is added as a pH regulator can accelerate the amino acid synthesis and the formation of callus in the tree.

Since the paint and the spreading agent in an ointment-like preparation according to the invention are highly water-absorbing, they effectively allow air and moisture to pass through the layer of the ointment applied to the tree and ensure breathing of the tissue cells of the tree while they suppress the activity of pathogenic germs. The components of the composite preparation operate synergetically to effectively protect the tree from the surroundings and, at the same time, suppress the activity of pathogenic microbes so that the formation of callus is accelerated in the tree. Note that the process of callus formation in the tree is retarded if powdery iron or powdery ferrous oxide is not added.

With a method according to the invention, the parts of a tree affected by necrosis are removed until almost all the germs causing the necrosis on the tree are killed. Then an ointment-like preparation encapsulated into microcapsules and comprising a mixture of an isothiocyanate such as allyl isothiocyanate or hinokitiol, a vinyl acetate resin, a coloring water paint, a powdery metal and a pH regulating agent is applied to the exposed areas of the tree after removing the affected parts so that the affected parts and the surrounding areas may not become necrosed by germs once again.

DESCRIPTION OF THE PREFERRED EMBODIMENTS

Now, the invention will be described by way of examples.

EXAMPLE 1

Fine particles of allyl isothiocyanate were dispersed into aqueous solution of a mixture of a urea formaldehyde resin prepolymer, a water soluble cationic urea resin and an anionic surfactant and an acidic catalyst was added to the solution to form a coating on the dispersed fine particles of allyl isothiocyanate for encapsulation thereof into microcapsules. Thereafter, the pH of the solution containing the dispersed microcapsules was regulated by means of a hydroxide of an alkaline earth metal and a monosaccharide was added to the solution to produce allyl isothiocyanate encapsulated into microcapsules (by means of a method according to Japanese Patent Publication No. 01-34649). Then, the encapsulated allyl isothiocyanate was mixed with the materials listed below to produce an ointment-like preparation.

| components | amount |
|---|---|
| microcapsules of allyl isothiocyanate | 2 to 5 cc |
| vinyl acetate resin | 3 kg |
| water-based acrylic paint (green) | 200 cc |
| acetic acid | 100 cc |
| powdery ion (fine powder) | 50 g |

Test

The obtained ointment-like preparation was then applied to the areas of a tree that had been exposed after removing certain parts of the tree affected by necrosis.

For the purpose of comparison, some of the remaining parts of the tree that had also been affected by necrosis were treated by respective (conventional) methods as described below for comparative examples and the treated parts were observed to obtain the results as listed in Table 1.

Comparative Example 1: Parts affected by necrosis were removed.

Comparative Example 2: Parts affected by necrosis were removed and, thereafter, the exposed areas were covered by mud and then a vinyl sheet.

Comparative Example 3: Parts affected by necrosis were removed and, thereafter, the exposed areas and the surrounding areas were treated by applying a 1,000 times diluent of TOPZIN M.

TABLE 1

| days | Example 1 | Comp. Examp. 1 | Comp. Examp. 2 | Comp. Examp. 3 |
|---|---|---|---|---|
| 0 | no change | no change | not observable | no change |
| 10 | no change | no change | not observable | no change |
| 30 | A large number of 1 to 2 mm particles appeared around the removed parts. | no change | not observable | 1 to 2 mm particles were gradually formed around the removed parts. |
| 40 | The particles gradually changed to 3 to 5 mm large pieces of callus. | 1 to 3 mm particles were gradually formed around the removed parts. | not observable | The particles started to grow into 3 to 5 mm large pieces of callus. |
| 60 | The pieces of callus mutually combined to become 8 to 35 mm large. | The particles started to grow into 3 to 5 mm large pieces of callus | 3 to 5 mm particles were found. The necrosis was completely cured. | The particles grew into 5 to 10 large pieces of callus. |
| 70 | The callus rapidly grew to become 25 to 80 mm large. | The particles grew into 5 to 10 mm large pieces of callus. | The particles grew into 5 to 10 mm large pieces of callus. | The particles grew into 5 to 15 mm large pieces of callus. |

As seen from Table 1 above, the ointment-like preparation of Example 1 was more effective than any of the tested conventional techniques (Comparative Examples 1 through 3) in suppressing the activity of pathogenic germs of plant necrosis and accelerating the formation of callus on the parts of a tree affected by necrosis.

The ointment-like preparation of Example 1 was also effective in the bark regeneration on the affected parts.

The method of Example 1 was advantageous in that, along with the doromaki method of Comparative Example 1, it did not contaminated soil nor air when compared with Comparative Example 3.

EXAMPLE 2

Fine particles of hinokitiol were dispersed into aqueous solution of a mixture of a urea formaldehyde resin prepolymer, a water soluble cationic urea resin and an anionic surfactant and an acidic catalyst was added to the solution to form a coating on the dispersed fine particles of hinokitiol for encapsulation thereof. Thereafter, the pH of the solution containing dispersed microcapsules was regulated by means of a hydroxide of an alkaline earth metal and a monosaccharide was added to the solution to produce hinokitiol encapsulated in microcapsules. Then, the encapsulated hinokitiol was mixed with the materials listed below to produce an ointment-like preparation.

| components | amount |
| --- | --- |
| microcapsules of hinokitiol | 2 to 5 cc |
| vinyl acetate resin | 3 kg |
| water-based acrylic paint (green) | 200 cc |
| acetic acid | 100 cc |
| powdery iron (fine powder) | 50 g |

The obtained ointment-like preparation was then applied to the areas of a tree that had been exposed after removing certain parts of the tree affected by necrosis to obtain the results similar to those of Example 1.

EXAMPLE 3

The root of a cherry tree was cut for transplantation and then the ointment-like preparation of Example 1 was applied to the cut surfaces. After transplanting, the root of the tree started producing shoots on the cut surfaces in 1 to 2 months.

EXAMPLE 4

The ointment-like preparation of Example 1 was applied to a surrounding area of a graft of two different trees that had been believed to be mismatched for grafting to prove that the preparation was good for such grafting.
Industrial Applicability A method of protecting a tree by using an ointment-like preparation according to the invention is advantageous compared to conventional methods of necrosis prevention in that it can effectively suppress the activity of pathogenic microbes of necrosis on a tree for a prolonged period of time by applying it only once after removing the affected parts of the tree. It is particularly advantageous compared to the doromaki method because the time required for treatment is far longer for the doromaki method.

An ointment-like preparation for the protection of a tree according to the invention is effective for the generation of the root of a tree that has been cut for transplantation. It also make it possible to graft two different trees that have been believed to be mismatched for grafting.

Additionally, since the substance contained in an ointment-like preparation according to the invention for suppressing the activity of pathogenic microbes is a compound that has been widely used as an additive for processing food, it is far safer to the health compared to conventional preparations used for the prevention of necrosis.

Finally, an ointment-like preparation for the protection of a tree according to the invention comprises components that can synergetically accelerate the formation of callus and vitalize the tree to which it is applied.

What is claimed is:

1. A composition which is an ointment and which is effective to protect a tree against disease, comprising:
   allyl isothiocyanate;
   vinyl acetate resin as a spreading agent;
   water-based colored paint;
   metallic powder which is finely divided and which is one of iron or ferrous oxide; and
   pH regulating agent.

2. The composition according to claim 1, comprising:
   from 0.05 to 1.0% by weight of encapsulated allyl isothiocyanate which is microencapsulated with a coating material;
   from 70 to 90% by weight of the vinyl acetate resin as a spreading agent;
   a water-based colored paint;
   from 1 to 10% by weight of metallic powder which is finely divided and which is one of iron or ferrous oxide; and
   from 1 to 10% by weight of a pH regulating agent.

3. The composition according to claim 1, wherein the water-based colored paint is an acrylic paint, wherein the metallic powder is ferrous oxide, and wherein the pH regulating agent is acetic acid.

4. The composition according to claim 1, wherein the allyl isothiocyanate is finley divided and encapsulated with a coating material comprised of cyclodextrin, and has the form of microcapsules.

5. The composition according to claim 4, wherein the water-based colored paint is an acrylic paint, wherein the metallic powder is ferrous oxide, and wherein the pH regulating agent is acetic acid.

6. The composition according to claim 1, wherein the allyl isothiocyanate is present as fine particles encapsulated with a coating material comprised of a reaction product of a urea formaldehyde resin prepolymer; a water soluble cationic urea resin; an anionic surfactant; and an acidic catalyst, and has the form of microcapsules, the encapsulation being accomplished by:
   providing an aqueous solution comprised of water; a mixture of a urea formaldehyde resin prepolymer; a water soluble cationic urea resin; and an anionic surfactant;
   dispersing the fine particles of the allyl isothiocyanate into the aqueous solution; and
   adding an acidic catalyst to the aqueous solution to cause formation of a coating of the coating material on the dispersed fine particles of allyl isothiocyanate, whereby the allyl isothiocyanate is encapsulated with the coating material.

7. The composition according to claim 6, wherein the water-based colored paint is an acrylic paint, wherein the metallic powder is ferrous oxide, and wherein the pH regulating agent is acetic acid.

8. The composition according to claim 1, wherein the water-based colored paint is an acrylic paint, wherein the metallic powder is ferrous oxide, and wherein the pH regulating agent is acetic acid.

9. A composition which is an ointment and which is effective to protect a tree against disease, consisting essentially of:

from 0.05 to 1.0 by weight of encapsulated allyl isothiocyanate which is microencapsulated with a coating material;

from 70 to 90% by weight of a vinyl acetate resin as a spreading agent;

a water-based colored paint;

from 1 to 10% by weight of metallic powder which is finely divided and which is one of iron or ferrous oxide; and from 1 to 10% by weight of a pH regulating agent.

10. The composition according to claim 9, wherein the water-based colored paint is an acrylic paint, wherein the metallic powder is ferrous oxide, and wherein the pH regulating agent is acetic acid.

11. A method of protecting a tree, comprising:

removing parts of the tree which are one of susceptible to necrosis from pathogenic microbes or affected by necrosis and leaving exposed tree surfaces; and applying to the exposed tree surfaces the composition according to claim 1.

12. The method according to claim 11, wherein the allyl isothiocyanate is present as fine particles encapsulated with a coating material and has the form of microcapsules.

13. The method according to claim 12, wherein the coating material is comprised of cyclodextrin.

14. The method according to claim 12, wherein the coating material is comprised of a reaction product of a urea formaldehyde resin prepolymer; a water soluble cationic urea resin; an anionic surfactant; and an acidic catalyst, and has the form of microcapsules, and wherein the method further comprises encapsulating the allyl isothiocyanate by:

providing an aqueous solution comprised of water; a mixture of a urea formaldehyde resin prepolymer; a water soluble cationic urea resin; and an anionic surfactant;

dispersing the allyl isothiocyanate present in fine particles into the aqueous solution; and adding an acidic catalyst to the aqueous solution to cause formation of a coating of the coating material on the dispersed fine particles of allyl isothiocyanate, whereby the allyl isothiocyanate is encapsulated with the coating material.

15. A method of protecting a tree, comprising:

removing parts of the tree which are one of susceptible to necrosis from pathogenic microbes or affected by necrosis and leaving exposed tree surfaces; and applying to the exposed tree surfaces the composition according to claim 9.

\* \* \* \* \*